(12) United States Patent
Basaglia

(10) Patent No.: US 8,684,927 B2
(45) Date of Patent: Apr. 1, 2014

(54) MEDICAL MACHINE FOR FLUID TREATMENT

(75) Inventor: Gianni Basaglia, Mirandola (IT)

(73) Assignee: Gambro Lundia AB, Lund (SE)

( * ) Notice: Subject to any disclaimer, the term of this patent is extended or adjusted under 35 U.S.C. 154(b) by 560 days.

(21) Appl. No.: 12/991,763

(22) PCT Filed: Apr. 27, 2009

(86) PCT No.: PCT/IB2009/005386
§ 371 (c)(1),
(2), (4) Date: Nov. 9, 2010

(87) PCT Pub. No.: WO2009/136243
PCT Pub. Date: Nov. 12, 2009

(65) Prior Publication Data
US 2011/0066693 A1    Mar. 17, 2011

(30) Foreign Application Priority Data
May 9, 2008    (IT) .............................. MI2008A0845

(51) Int. Cl.
*A61B 5/00*        (2006.01)
*G06F 19/00*       (2011.01)

(52) U.S. Cl.
CPC ........ *G06F 19/3406* (2013.01); *G06F 19/3468* (2013.01)
USPC .......................................................... 600/301

(58) Field of Classification Search
USPC ................... 600/300–301; 705/2–4; 340/539.12–539.14
See application file for complete search history.

(56) References Cited

U.S. PATENT DOCUMENTS

| | | | |
|---|---|---|---|
| 6,406,426 B1 | 6/2002 | Reuss et al. | |
| 6,730,026 B2 | 5/2004 | Christ et al. | |
| 6,938,203 B1 * | 8/2005 | Dimarco et al. | ............... 715/209 |
| 7,755,488 B2 * | 7/2010 | Dvorsky | ..................... 340/572.1 |
| 7,933,780 B2 * | 4/2011 | De La Huerga | ................... 705/2 |
| 8,126,728 B2 * | 2/2012 | Dicks et al. | ......................... 705/2 |
| 8,360,977 B2 * | 1/2013 | Marttila et al. | ............... 600/371 |
| 2002/0082728 A1 | 6/2002 | Mueller et al. | |
| 2002/0099283 A1 | 7/2002 | Christ et al. | |
| 2002/0128801 A1 | 9/2002 | Okuno et al. | |
| 2003/0128126 A1 | 7/2003 | Burbank et al. | |
| 2004/0010425 A1 * | 1/2004 | Wilkes et al. | ...................... 705/3 |

(Continued)

FOREIGN PATENT DOCUMENTS

| | | |
|---|---|---|
| EP | 1 107 159 A2 | 6/2001 |
| EP | 1 623 666 A2 | 2/2006 |

(Continued)

*Primary Examiner* — Bill Thomson
*Assistant Examiner* — Bobby Soriano
(74) *Attorney, Agent, or Firm* — Pearne & Gordon LLP

(57) ABSTRACT

A medical machine for fluid treatment comprises a module (400) for management and sending of signal messages containing information relating to means (3) for fluid treatment. The module (400) comprises means (401) for determining a form for sending a signal message which is selectable automatically or manually from among a plurality of predefined forms. The module further comprises means (403) for generating contents of the signal message which comprise information (404*a*, 404*b*, 404*c*, 404*d*) relating to means (3) for fluid treatment; the contents (412) are created by selecting, for example via touch buttons on a touch screen, from among a selectable plurality of types of predefined contents (404*a*, 404*b*, 404*c*, 404*d*) and associating the relative data (405*a*, 405*b*, 405*c*, 405*d*) to the selected type; the module further comprises means (406) for determining at least an addressee to whom to send the signal message.

30 Claims, 7 Drawing Sheets

(56) References Cited

U.S. PATENT DOCUMENTS

| | | |
|---|---|---|
| 2004/0015132 A1* | 1/2004 | Brown .................... 604/131 |
| 2004/0078231 A1* | 4/2004 | Wilkes et al. .................. 705/2 |
| 2004/0122702 A1* | 6/2004 | Sabol et al. ................... 705/2 |
| 2004/0180810 A1* | 9/2004 | Pilarski ......................... 514/3 |
| 2005/0027567 A1* | 2/2005 | Taha ............................. 705/2 |
| 2005/0108057 A1* | 5/2005 | Cohen et al. .................. 705/3 |
| 2005/0143632 A1* | 6/2005 | Elaz et al. ................... 600/301 |
| 2005/0182655 A1 | 8/2005 | Merzlak et al. |
| 2005/0267402 A1 | 12/2005 | Stewart et al. |
| 2006/0010090 A1* | 1/2006 | Brockway et al. ............. 706/46 |
| 2006/0015015 A1* | 1/2006 | Kawamoto et al. ........... 600/300 |
| 2006/0047538 A1* | 3/2006 | Condurso et al. .............. 705/3 |
| 2006/0049936 A1 | 3/2006 | Collins et al. |
| 2006/0116908 A1* | 6/2006 | Dew et al. ..................... 705/2 |
| 2006/0253301 A1 | 11/2006 | Simms et al. |
| 2007/0015975 A1* | 1/2007 | Faries et al. ................. 600/300 |
| 2007/0168228 A1* | 7/2007 | Lawless ......................... 705/2 |
| 2007/0233206 A1 | 10/2007 | Frikart et al. |
| 2007/0257788 A1* | 11/2007 | Carlson et al. ............... 340/506 |
| 2008/0001735 A1* | 1/2008 | Tran .......................... 340/539.22 |
| 2008/0046286 A1* | 2/2008 | Halsted ........................... 705/2 |
| 2008/0079558 A1* | 4/2008 | Dorgelo et al. .............. 340/506 |
| 2008/0091466 A1* | 4/2008 | Butler et al. .................... 705/2 |
| 2008/0126127 A1* | 5/2008 | Bobroff .......................... 705/2 |
| 2008/0133265 A1* | 6/2008 | Silkaitis et al. ................ 705/2 |
| 2008/0162352 A1* | 7/2008 | Gizewski ...................... 705/50 |
| 2008/0194924 A1* | 8/2008 | Valk et al. .................... 600/301 |
| 2008/0208631 A1* | 8/2008 | Morita et al. ................... 705/3 |
| 2008/0215360 A1* | 9/2008 | Dicks et al. .................... 705/2 |
| 2008/0242952 A1* | 10/2008 | Jung et al. .................... 600/300 |
| 2008/0249386 A1* | 10/2008 | Besterman et al. ........... 600/365 |
| 2008/0249808 A1* | 10/2008 | Jung et al. ..................... 705/3 |
| 2008/0294018 A1* | 11/2008 | Kurtz et al. ................... 600/301 |
| 2008/0294462 A1* | 11/2008 | Nuhaan et al. .................. 705/3 |
| 2009/0012798 A1* | 1/2009 | McConnell et al. ............. 705/1 |
| 2009/0048866 A1* | 2/2009 | Mahesh et al. .................. 705/2 |
| 2009/0088613 A1* | 4/2009 | Marttila et al. ............... 600/309 |
| 2009/0138281 A1* | 5/2009 | Hacker ........................... 705/3 |
| 2009/0157426 A1* | 6/2009 | Malec et al. .................... 705/3 |
| 2009/0216556 A1* | 8/2009 | Martin et al. ................... 705/3 |
| 2009/0234672 A1* | 9/2009 | Dicks et al. .................... 705/3 |

FOREIGN PATENT DOCUMENTS

| | | |
|---|---|---|
| EP | 1 765 435 | 3/2007 |
| EP | 1 818 843 A2 | 8/2007 |
| EP | 1 877 944 | 1/2008 |
| WO | 2005/118028 A1 | 12/2005 |
| WO | 2006/119370 A2 | 11/2006 |

* cited by examiner

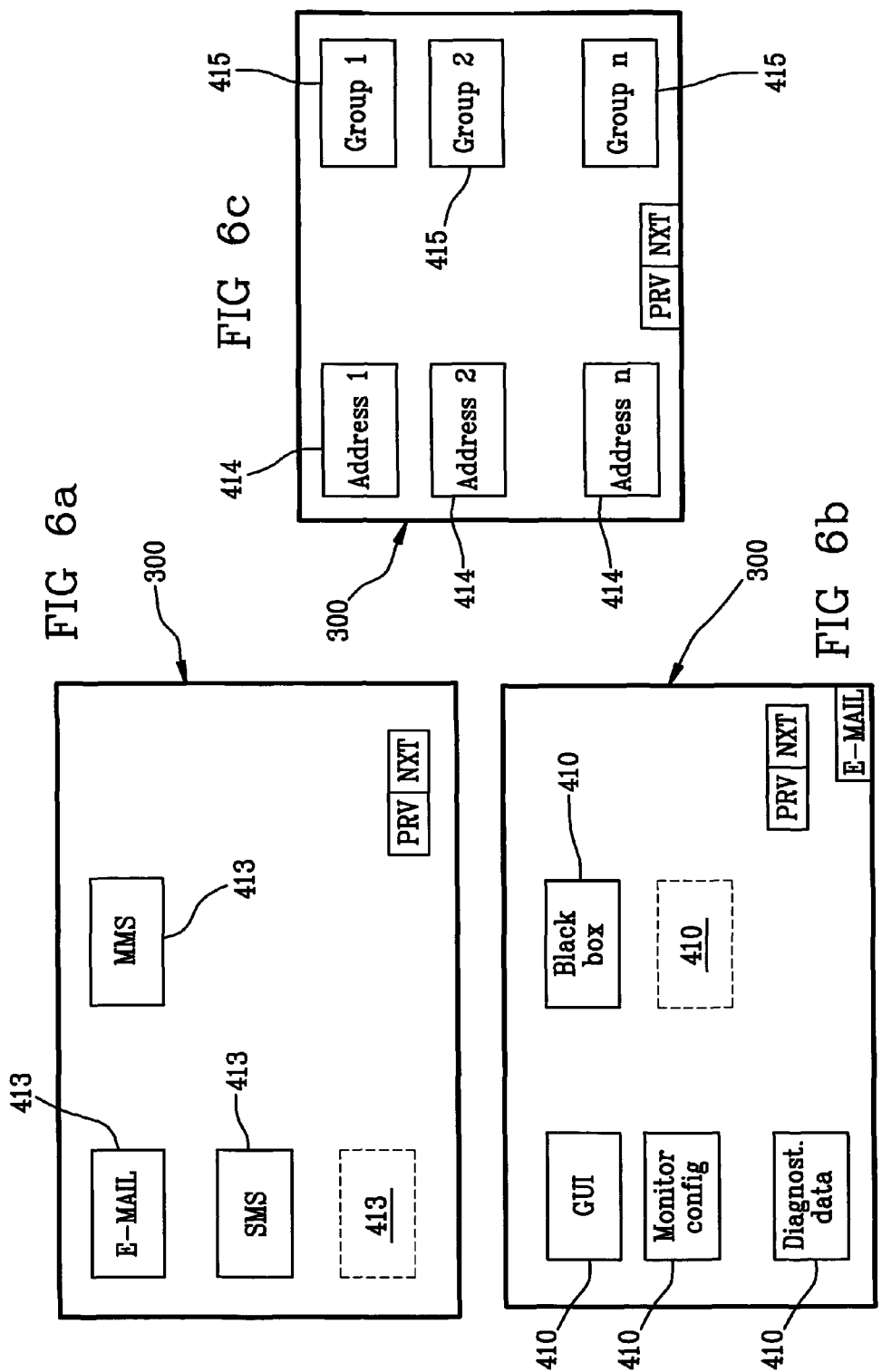

MEDICAL MACHINE FOR FLUID TREATMENT

BACKGROUND OF THE INVENTION

The invention relates to a medical apparatus and in particular a machine for extracorporeal treatment of a fluid, i.e. a patient's blood.

As is known, machines for treatment of blood, such as for example machines for treatment of kidney failure or liver insufficiency or machines for plasmapheresis, i.e. machines for other types of fluid treatment, are provided with special means for treating a fluid in general comprising appropriate sensors and actuators which enable the cited treatment to be carried out.

In general all the above-mentioned machines have in common a presence of a control unit which is destined to send control signals and to receive data from the sensors and/or actuators for monitoring and controlling the treatment.

Obviously for interaction with the machines, the operator can provide commands to the control unit, as well as view machine data and parameters in order to monitor its functioning.

To this end, usually at least a device for entering data is included which can be constituted by a keyboard, a mouse, suitable buttons and activations, or even a touch screen; there is also always a special display for visualising the data requested received from the sensors and/or relating to the actuators.

As the above concerns medical machines, those briefly described above are provided with special device for generating and managing alarms and signals which relate to a plurality of levels and different types of alerts.

For example, document US 2003128126 describes a medical machine in which an alarm condition detector establishes the presence of a risk situation and an alarm controller generates the alert signal.

The alert signal is directly correlated to the importance of the alarm that has gone off, and can be pre-configured as an audio alarm, or a flashing or coloured light alarm, or an e-mail message alarm, a local network message or even a telephone call to a doctor/operator.

Document US 2002099283, also relating to a medical system for monitoring the to value of blood coagulation measured in a patient teaches notifying a technician, i.e. a doctor, etc., via various types of message such as telephone, e-mail, normal post etc., according to the urgency and type of message to be sent.

Devices for management and despatch of signalling messages, as briefly described above, though well achieving the aims they set for themselves, are however affected by some operating limits and/or drawbacks and have shown themselves to be susceptible to improvement under various aspects.

Firstly, devices for managing and sending signal messages are non-configurable (or in any case are hard to configure) if not during the stage of predisposition of the machine, and typically by a specialised technician.

In general, on verifying the situation of danger the known system automatically implements the signals paired with the type of alarm.

The nursing staff, doctors or patient cannot usually intervene rapidly on the medical machine to manage or configure signalling of an alarm in a way which is most suited to a particular situation that has arisen.

Further, known systems do not enable, if not a priori, establishing a type of despatch and the correct target (in terms of expert personnel) of a signal, nor is it usually possible to intervene in order to vary and/or implement the information sent.

AIM AND SUMMARY OF THE INVENTION

The aim of the present invention is thus substantially to obviate the above-cited drawbacks.

A first aim of the invention is to make available a medical machine provided with a module for managing and sending message signals which enable guaranteeing an excellent functioning reliability of the alarm signal, at the same time affording the possibility for the personnel to intervene during the sending of the signals themselves.

A further aim of the present invention is to provide a medical machine which enables customisation, of the signals management, both in terms of contents and in terms of the transmission format, and also in terms of the addressees of the information.

A further aim is to enable management and sending of signals at any moment without an automatic machine alarm or intervention situation necessarily having been triggered.

An auxiliary aim of the invention is to enable a differentiated management of the sending of the signals according to the addressee and/or according to the type of alarm and/or signalling necessary.

These and other aims, which will better emerge during the course of the following description, are substantially attained by a medical machine for fluid treatment according to the accompanying claims.

Further characteristics and advantages will better emerge from the detailed description that follows of a preferred though not exclusive embodiment thereof, according to the invention.

BRIEF DESCRIPTION OF THE DRAWINGS

The preferred embodiment will be described herein below with reference to the accompanying figures of the drawings.

FIGS. 6a-6c are schematic views of a graphic user interface shown by the display of the medical machine of FIG. 4.

DETAILED DESCRIPTION OF SOME PREFERRED EMBODIMENTS

Figure 1:
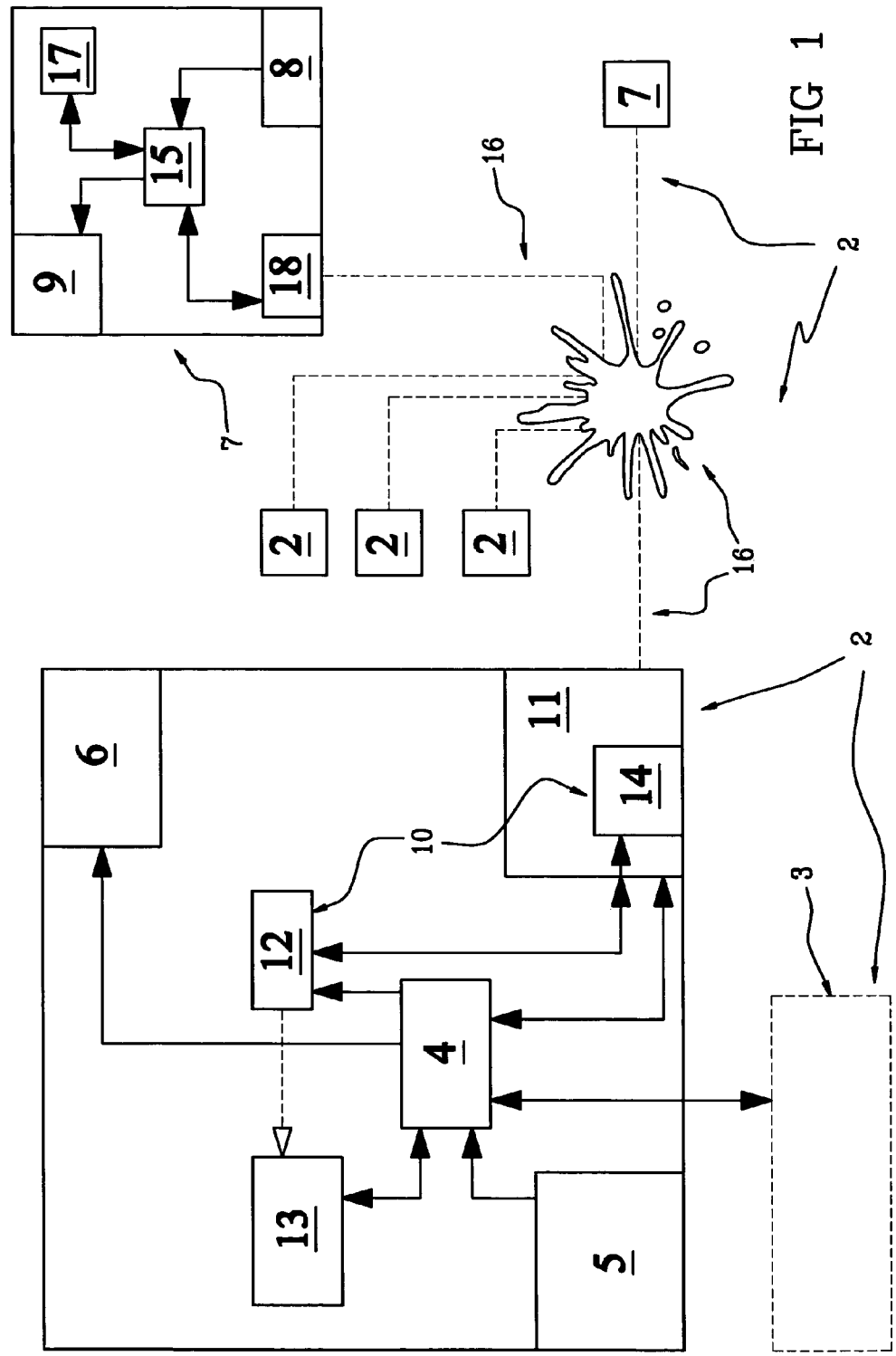
FIG. 1 is a schematic view of an apparatus of the present invention, in which the medical machine is monitored/controlled by a remote unit.
Figure 1A:
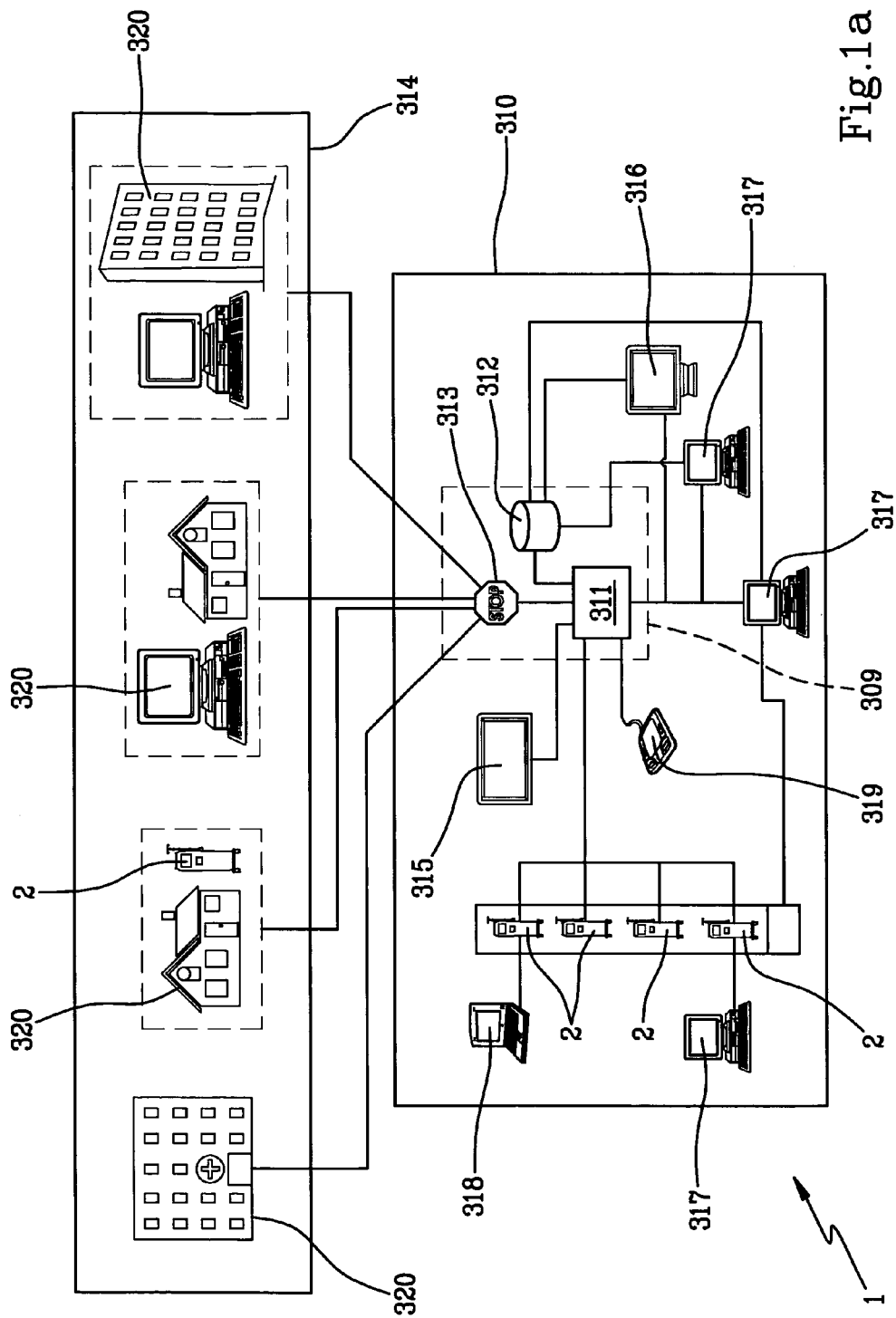
FIG. 1a schematically illustrates a medical network including machines that implement the inventive idea of the invention.

FIG. 1a is a schematic view of a medical network which incorporates the object of the present invention.

The inset 310 provides an example of a first portion of the medical network, delimiting the apparatus of the network which are typically present internally of a same building, such as a hospital, a dialysis unit, or a clinic.

A plurality of medical machines 2 are included in the first portion of network 310, and in particular medical machines suitable for fluid treatment.

The medical machines 2 can all be connected to one another and to a central server 309.

The central server 309 can comprise at least a computer server 311, a database 312, and means for access 313 to the external portion 314 of the medical network 1.

As can be seen, still schematically, there is also at least a visual access terminal (and usually a plurality) 316 in order to enable the personnel (in particular the nursing staff) an access to the data contained in the central server 309 and therefore access to the net.

A plurality of desktop personal computers 317 will be connected to the network, which will have access to the central server 309, and to the medical machines 2 as will be better clarified herein below.

Access can also be given to other apparatus such as handheld computers 319 or laptops 318, directly connectable to the server 309 and/or medical machines 2, as shown in FIG. 1*a*.

The external portion of the network 314 includes the presence of a plurality of remote accesses 320 which might be constituted by terminals for technicians working on the maintenance and/or control of the functionality of the medical network, terminals for doctors, terminals or even patients' medical machines, or other hospitals, clinics or medical units.

Access can also be given to a domiciled medical machine, not necessarily connected to a hospital network. In this case the remote access can be effected, for example, via a remote computer provided with an appropriate web browser able to communicate with a web server provided on the domiciled medical machine.

In this case the network architecture will, in the most elementary form, be constituted by at least a medical machine which will be provided with its own network address and by a remote terminal which will connect to the machine via the address.

Obviously the use of the internet as a net infrastructure will enable creating very varied network architectures according to the needs of each individual case.

In the light of the above, a medical machine 2 will now be described which is suitable for fluid treatment, which can be used in the medical network 1 as briefly described above.

The machine can be, for example, a machine for blood treatment, such as a machine for treatment of kidney failure (for example a hemo(dia)filtration or dialysis machine, for chronic or intensive therapy), or liver insufficiency or a machine for plasmapheresis or in any case any other type of medical machine which is suitable for fluid treatment.

In the following, reference will be made to a medical machine for extracorporeal blood treatment in its essential components of known type and therefore only partially described.

The apparatus for fluid treatment comprises suitable means for blood treatment 3.

In particular the means 3 comprise a hydraulic circuit 100. An example of a hydraulic circuit is schematically shown in FIG. 2.

Figure 2:
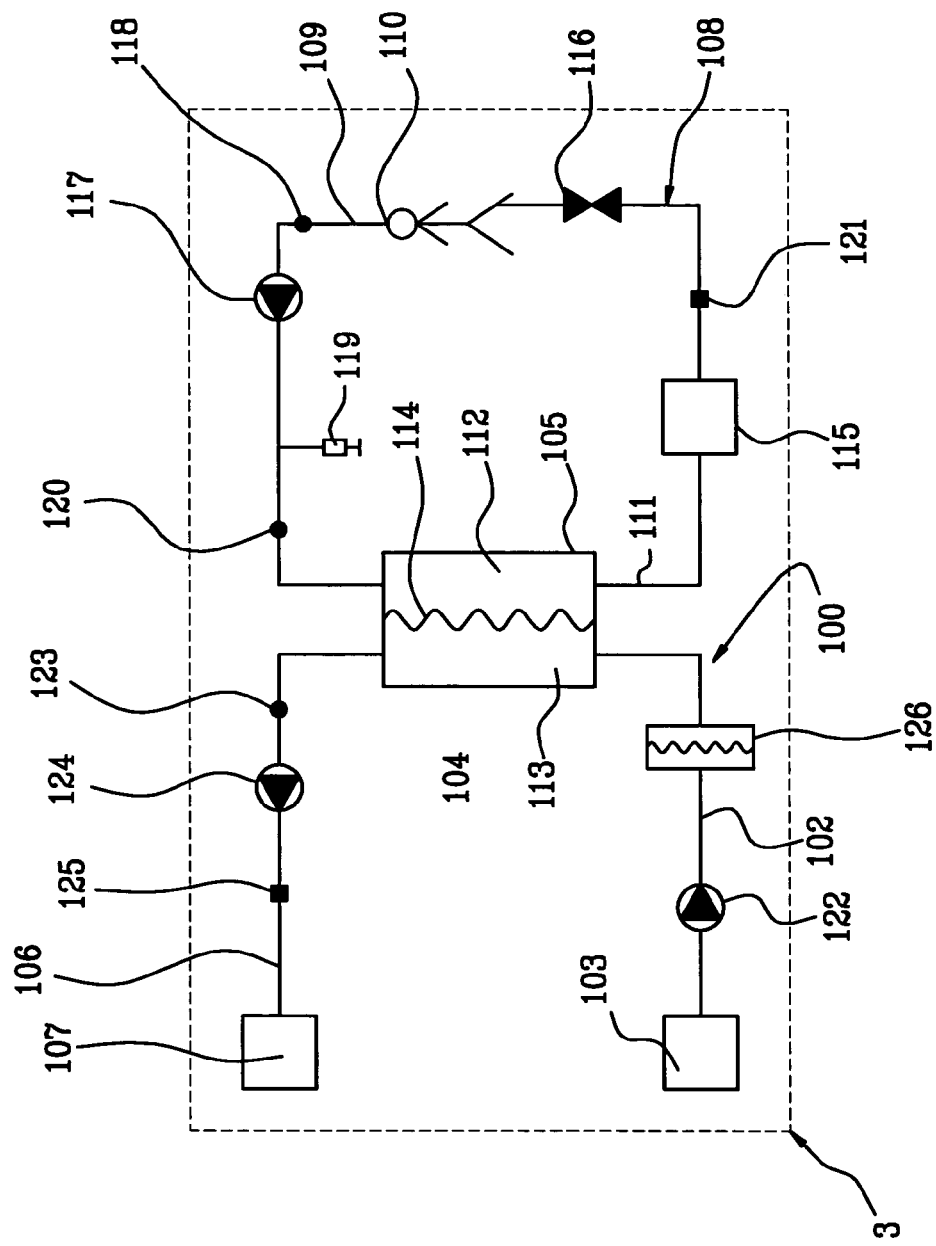
FIGS. 2 and 3 schematically illustrate, in a first and a second embodiment, means for fluid treatment, part of the medical machines of FIG. 1.

Note that the specific structure of the hydraulic circuit 100 is irrelevant for the purposes of the present invention, so different circuits to the one specifically shown in FIG. 2 can be involved, according to functional and design needs for each single medical apparatus.

The hydraulic circuit 100 optionally exhibits at least a supply channel 102, destined for the transport of a treatment liquid of at least a source 103 towards a treatment station 104, where one or more blood treatment units 105 operate.

The circuit 100 further comprises at least a discharge channel 106 destined to transport a used liquid from the treatment station 104 towards an evacuation zone, schematically denoted by 107 in FIG. 2.

It should be noted that the supply channel 102 is destined to cooperate with means for moving a fluid, such as at least a pump 122, for example a positive displacement pump, such as in particular a peristaltic pump, or a gear or diaphragm pump.

A branch can be present downstream of the pump 122 and along the circulation direction, which divides the primary sterile fluid circuit into an inlet branch and an infusion branch (not illustrated but of known type).

The infusion branch is connected to the blood removal line (arterial line) and/or the blood return line (venous line) of the blood circuit and enables an infusion to be obtained directly into the blood (before and/or after the blood treatment unit 105) using sterile fluid.

The input branch brings the sterile fluid directly to the blood treatment stations 104 for exchange through the membrane 114.

Obviously selector means (for example a valve element and/or means for moving, such as one or more pumps) will be present for determining the percentage quantities of fluid flow in the infusion branch and the entry branch.

The sterile fluid for dialysis thus enters the discharge channel 106 of the circuit and crosses a pressure sensor 123 provided for control of the functioning of the line.

There are therefore further fluid movement means present, for example a drainage pump 124 which can control the flow in the discharge channel 106 of the circuit.

The drainage pump 124 can, in general, be a positive displacement pump, such as for example a peristaltic pump, or a gear pump, or a diaphragm pump.

The fluid to be eliminated thus crosses a blood leak detector 125 and is conveyed towards the evacuation zone 107.

The treatment fluid (dialysis fluid or replacement fluid) can be purified before use by one or more ultrafilters 126.

The hydraulic circuit 100 cooperates with a blood circuit 108 which is also schematically represented in FIG. 2 in its basic components.

The specific structure of the blood circuit is also not fundamental with reference to the present invention, and thus, with reference to FIG. 2, a brief description of a possible embodiment of the circuit is provided, which should however be considered to be provided purely by way of non-limiting example.

The blood circuit 108 of FIG. 2 comprises an arterial line 109 for removing blood from a vascular access 110 of a patient and a venous line 111 predisposed to return the treated blood to the vascular access.

The blood circuit of FIG. 2 further comprises a first chamber, or blood chamber 112, of the blood treatment unit 105 whose second chamber 113 is connected to the hydraulic circuit 100.

In greater detail, the arterial line 109 is connected to the inlet of the blood chamber 112, while the venous line 111 is connected in outlet to the blood chamber 112.

In turn, the supply channel 102 is connected in inlet to the second chamber 113, while the discharge channel 106 is connected in outlet to the second chamber.

The blood treatment unit 105, for example a dialyser or an ultrafilter or a plasma filter or a hemofilter or a hemodiafilter, comprises, as mentioned, the two chambers 112 and 113, which are separated by a semi-permeable membrane 114, for example a hollow-fibre or plate-type membrane.

A blood pressure sensor 118 is located on the arterial line 109 along the circulation direction of the blood from the removal zone (vascular access) towards the blood treatment unit 105. The arterial line 109 is further connected to a device for administering an anticoagulant 119, for example a syringe pump for providing appropriate anticoagulant doses (heparin).

The arterial line can thus be provided, optionally, with a further pressure sensor 120 (arranged between a pump 117 and the unit 105) for surveying the correct flow internally of the blood circuit.

The blood circuit can also comprise one or more air separators 115: the example of FIG. 2 shows a separator 115 on the venous line 111, upstream of a safety valve 116.

The treated blood, exiting from the air separator device 115, crosses an air bubble sensor 121, provided to check for the absence of dangerous formations internally of the treated blood which must be returned into the patient's blood circuit.

In particular, should the air bubble sensor reveal the presence of faults in the blood flow, the machine, via the safety valve 116 (which might be a cock, a clamp or the like) it would be able immediately to block blood passage in order to prevent any type of consequence to the patient.

The valve 116 can always be closed in the venous line should, for example for safety reasons, it become necessary to interrupt blood return to the vascular access 110.

The means 3 for fluid treatment can also comprise one or more blood pump 117, for example positive displacement pumps such as peristaltic pumps; in the example of FIG. 2 there is a pump 117 on the arterial line 109.

In general, the hydraulic circuit 100 is housed internally of a chamber in the machine body, while the blood circuit 108 is borne on a front panel of the machine body which also supports the peristaltic pump or pumps 117.

The treatment unit 105 can be removable physically supported, by rapid-attachment means (of known type) arranged, for example, on a lateral wall of the machine structure itself. The treatment unit 105, in operating conditions of blood treatment, is connected both to the hydraulic circuit and to the blood circuit as already briefly mentioned.

As is obvious and indeed known, the means 3 for fluid treatment comprise the cited sensors for detecting functioning parameters of the medical machine 2 and also the cited actuators for intervening in order to modify the functioning parameters of the machine 2.

Each medical machine 2 in general comprises a control unit 4 which is programmed at least to send command signals and to receive data from the means 3 for fluid treatment.

The control unit 4 is thus active at least on the blood circuit and in particular on the pressure sensor 118, on the blood pump 117, on the heparin infusion device 119, on the further pressure sensor 120 as well as on the device for detecting the presence of air bubbles 121 and on the closing element 116.

The control unit 4 will be active on the pump 122, on any selector means present, on the pressure sensor 123, on the drainage pump 124 and will also receive information from the blood leak detector 125.

Further, the control unit 4 is set up to control the hydraulic circuit 100 of the sterile fluid and in particular will receive in input the data read off by any balances present on the machine relating to the weight of the various containers which may be in use on the machine.

Obviously, apart from the control of the sensors and the actuators, the control unit 4 may be predisposed to receive and control further sensors and actuators present on the machine in order to guarantee and monitor the functioning thereon.

The machine for extracorporeal treatment may be provided with a fluid balance system, of the type used in a machine for hemodialysis and hemo(dia)filtration, for control of the patient's weight loss during the treatment, for example a flow-meter type, or a variable-volume volumetric chambers system, or a system including balances, or other systems of known type.

The machine can be provided with a system, of known type, for on-line preparation of the treatment fluid (for example dialysis fluid and/or replacement fluid) starting from water and concentrates, and/or a system (of known type) for degassing and/or heating the fluids running through the system itself, and/or a purification system having one or more treatment fluid ultrafiltration stages.

The machine can be provided with a disinfection/cleaning system (of known type, for example of a chemical or thermal type, supplied by a distribution network or a batch source of disinfecting agents/cleaners) of the hydraulic circuit 100.

Purely by way of example there might also be a liquid loss sensor destined to detect any eventual breakages or damage to the hydraulic circuit, which sensor will then send the data on directly to the control unit 4 for subsequent processing.

The control unit 4 can, for example, comprise one or more digital microprocessing units or one or more units of an analog and/or digital type.

In practice, in reference to the example of a microprocessor unit, once the unit has completed a special program (for example a program coming from outside the system or directly installed on the microprocessor), it is programmed by defining a plurality of functional modules or blocks which constitute means each predisposed to perform respective operations.

The medical machine is provided with at least a display 6 for viewing at least a part of the data received from the control unit 4 relating to the means for fluid treatment.

Further, the medical machine will be provided with at least one and in general a plurality of devices 5 for entering the data to be supplied to the control unit 4 in order to enable a user to generate the above-mentioned command signals for the means 3 for fluid treatment.

The devices for entering data can be of various natures and be constituted, even in combination, by a keyboard, a mouse, keys and buttons and activations, or even a touch screen.

In particular the display or screen of the medical machine 2 displays a graphic user interface (GUI) which provides an intuitively-comprehensible display of at least a part of the data received from the control unit 4 relating to the sensors and the actuators on the fluid treatment circuit.

Merely by way of non-limiting example, in a case in which a graphic user interface is used with a configuration of the touch screen, the display 6 itself will be divided into various areas exhibiting a plurality of touch keys and a plurality of pictograms, each for example associated to a relative touch key.

The expression "touch screen" relates to a screen for data output, also used for input by means of direct selection using the fingers of parts (touch keys) of the screen display to send the commands for performing the user's requested action to the control unit 4.

The use of a touch screen might for example configure the display and the device 5 for entering the data in a single element.

The main aim of a touch-screen display is that it makes the interface more intuitively simple use for the operator, and at the same time simplifies the use of the machine.

The medical apparatus advantageously also exhibits remote access and control means 10 which can enable a remote unit 7 to accede to data present in the medical machine and selectively take over control of a predetermined number of functions of the medical machine itself.

In general the remote access and control means 10 comprise at least a central control program 12 for enabling remote administration of the functions of the medical machine; the central control software 12 can be a VNC type program, and in particular a VNC server program.

In general, VNC programs (Virtual Network Computing) are open source with remote control and serve for remotely administrating a machine.

The VNC server will cooperate with the control unit 4 which, once the program has been run, will be programmed to define the access and control functions from a remote position.

Purely by way of example, the VNC server can be prestored on a memory bank 13 of the medical machine to which the control unit 4 will be able to accede.

Obviously the remote access and control means 10 will also comprise client control software 14 for interacting with the central control program 12 in order to enable the mentioned data exchange between the control unit 4 and the remote unit 7.

The client control software 14 will also optionally be of the VNC type and in particular VNC client.

Note that while the VNC server will in general be stored internally of the medical machine, the VNC client might be differently located.

The VNC client might for example be directly loaded on the remote control unit 7 which might be an electronic processor such as a computer, but also a hand-held computer or a smart-phone.

Alternatively the VNC client might be directly installed in an intermediate server, to which the remote unit 7 will accede and which in turn will initiate the communication with the medical machine.

In a preferred embodiment it will also be possible for the VNC client to be loaded directly in the medical machine 2 such that it is possible to accede to monitoring and control functions remotely by using a remote control unit 7 without any type of dedicated software, for example a normal processor, a hand-held unit or a smart-phone, as long as it is on-line with the medical machine to be controlled and/or monitored.

For this purpose the medical machine will be provided with a web server 11 operatively cooperating with the control unit 4.

In general a web server is a program which on request of a browser 18 requests one or more web pages (often written in HTML).

A web server is also usually (though not necessarily) provided with a fixed IP address on the net such as to be able to gain remote access more simply.

The data sent from the web server travel in a processor network, transported by the cited http protocol (or equivalent protocols).

The web server 11 of the medical machine 2 is configured to provide a predetermined number of remotely-accessible web pages via the connecting means 16. The web server 11 can contain the predetermined number of web pages or it can generate them at the necessary moment and send them.

In particular the web server 11 can generate these web pages in real time and can therefore transmit them to a user (for example via the connecting means 16), particularly on request of the user him or herself. This enables system is security to be increased, especially because it prevents undesired breaches by hackers onto any pages stored in a memory. In effect the web server 11, in order to reduce the risk of fraudulent break-ins from the outside, might not necessarily operate by storing data (web pages), but via generation on demand (in real-time) of data (i.e. web pages) requested.

In detail, the medical machine is predisposed to be connected to the internet in particular with a fixed IP address such that the web pages thereof are selectively accessible.

A general characteristic of a web server publishing web pages, i.e. an internet website, is that of being available on the internet with a certain degree of continuity for those who need to access the site.

In this sense the connecting of the medical machine could be defined as a permanent connection which denotes the normally-active connection to the internet which characterises web-sites and distinguishes them from convention client serves which, on the contrary, must set up a new connection each time exchange of data is required, with any remote processor.

It is clear that for breakdowns, maintenance or other extremely practical matters, the connection between the machine and the internet can be interrupted, without altering the characteristic of substantial temporal continuity of the connection.

The connecting means 16 advantageously comprise an auxiliary memory, predisposed to contain a permanent IP address, independently associated to the medical machine; the IP address is used for the above-mentioned permanent connection to the internet.

A further fundamental characteristics of an internet site is that the server which physically incorporates the contents of the site is identified by an IP address (Internet Protocol) so that the server can be correctly addressed by the various routers and providers constituting the internet.

The IP address is basically constituted by a 32-bit number, for the sake of simplicity usually a sequence of four numbers, each comprised between 0 and 255, and separated from the others by a dot (for example 192.168.9.112).

As indicated, IP addresses are used for identifying the actual physical machines in which the web pages are contained, together with the contents attached thereto, which constitute an internet site.

To enable net users to record the addresses of the various sites, each IP address is usually, but not necessarily, univocally associated to a domain name, i.e. a sort of name or title given to the site and indicating the contents of the site.

At the moment when a net user decides to connect to a predetermined internet site, she or he enters the name of the site or the IP address to be visited in the address bar of her or his browser.

In the case in question, the remote user enters the domain name or the IP address of the machine she or he wishes to contact.

The composition of the domain name constitutes the generation of the request signal; the domain name is immediately converted into the corresponding IP address, such that the request is correctly directed towards the medical machine 2.

This is made possible by the structure of the internet, internally of which the various nodes are able, via a series of pre-stored tables, to direct the signals to the pre-selected address.

A first table enables the addressee's IP address to be found, if the domain name associated thereto is known; the subsequent tables set up the distance link between the remote processor 7 and the medical machine, appropriately selecting the branches of the net to be used for the transmission.

Finally, a last database associates the IP address to a branch which is directly connected to the addressee computer, such that the data can be sent to it.

In the light of the above, it is clear how the dedicated association of a permanent IP address to the medical machine enables the machine to be visible to the users on the internet, and in particular the doctor, technician or remote user, to all effects just like a website which can be accessed independently of the physical position of the remote processor 7.

In some cases, for example, when the various servers and providers reorganise their internal databases with the aim of optimising the exploitation of the hardware and software resources and rendering net operation as efficient and possible, IP addresses associated to each site can be changed; this does not mean however that the IP address combined with a predetermined internet site cannot be defined as permanent, differently to the provisional code attributed to normal clients each time the client accesses the net via its provider.

The web pages provided (contained or generated in real-time) in the web server 11 of the medical machine are consultable via a web browser 18, i.e. a program which enables the users to view and interact with texts, images and other data contained in one or more web pages of a web server.

The web browser 18 is generally able to interpret the HTML code and display it in the form of a hypertext, enabling surfing of the web server pages.

The web server 11 in the medical machine 2 will be accessible via standard-type web browsers 18, commonly used for surfing the internet.

By way of example, the following browsers can be used: Internet Explorer, Mozilla Firefox, Opera or others besides, for access to the web server of each of the medical machines.

Usually, and advantageously, web pages of the web server comprise the client control software 14 such that it does not necessary have to be resident or have been downloaded previously on the remote processor for access to the medical machine.

Obviously the control software could be a compiled program, resident on the web page of the web server of the medical machine, for downloading, installing on the remote unit and thereafter being usable; however it has been found to be particularly advantageous to upload the program to the web page in the form of a specific language, for example a scripting language or an interpreted programming language (i.e. which is not compiled)—destined in general for use in system automation (batch) or applications (macros), or for use in the web pages.

Examples of scripting languages are JavaScript, VBScript, Shell scripting (Unix), Perl, PHP, Python e Ruby.

An example of an interpreted language is JavaApplets.

All of the above means that the client program 14, in scripting language or interpreted language, is directly and automatically executed (interpreted) by the web browser 18 without any need for intervention on the part of the user.

Having directly provided the web server 11 with the VNC client software 14 constitutes a considerable simplification of the monitoring and control procedures.

It should be noted that at least one of the web pages of the medical machine 2 reproduces the graphic user interface shown on the display 6 of the machine itself, apart from a plurality of further data and information relating to the medical machine.

In more detail, thanks to the remote access and control means 10 (which comprise the VNC server and the VNC client), the graphic user interface shown on the display 6 is reproduced in the web pages of the web server 11 and the reproduction is done practically in real-time.

In other words, the reproduction of the graphic user interface is updated at each predetermined time interval and/or at each predetermined change of at least a parameter represented in the graphic user interface itself.

The above-mentioned update of the graphic user interface can also be done as follows, with the aim of reducing the amount of work done by the controller. The display is subdivided into a plurality of regions (distinct monitoring regions) in which each region of the display is subjected to a monitoring; each time a change in the information reproduced in a certain region of the screen occurs, the update only for that region is sent.

The user can therefore, for example by means of an authentication with a password or similar authentication systems, access the web pages of the medical machine, receive a graphic representation which substantially coincides and is in real-time with the graphic representation of the user interface or GUI, and can also surf between the cited plurality of further data published in the web pages of the web server 11, such as for example information relating to the configuration of the machine (version of the programs loaded, cards installed on-board, etc.).

The user can also access the pages for data relating to maintenance (days since last check, or until next maintenance operation).

The user can receive information relating to the replacement of the ultrafilter (days since the last or before the next replacement of the ultrafilter, number of disinfection operations carried out since the last replacement, etc.).

Time/variation graphs can be viewed for some predetermined parameters, so that their progress can be monitored.

Access might be given to the alarm record of the machine (for example the last N alarms, the most frequent alarms, etc.).

Access can be given to data relating to the dates of disinfections performed on the machine, as well as to the history of control tests done by the machine in the context of preventive maintenance, as will be more fully described herein below.

As however previously mentioned, the remote access and control means 10 are not exclusively dedicated to enabling secure access to a plurality of data relating to the medical machine, but have also the function of enabling selective control of at least a predetermined number of functions of the machine itself. The controllable functions of the medical machine are multiple and can comprise, purely by way of example, pump velocity, heparin doses (or other substances), treatment operating parameters, such as the treatment times of the rate of ultrafiltration; further, among the controllable functions are the internal check or diagnostic check procedures, as are the updating or downloading of programs onto the machine.

In a non-exclusive preferred embodiment, the remote access and control means 10 enable the remote control unit 7 to take over complete control of the medical fluid treatment machine 2 such that a remote user can interact with the machine as if she or her were actually standing in front of the machine 2 controls.

Generally, for each remote connection, the user will have to be identified and the authentication will be done for example by means of entering the identification and corresponding password. In any case remote identification might be done in different ways, possibly even in combination, and according to the required level of security. Identification systems can be used such as cards with chips, or contactless, means for biometric recognition (fingerprints, iris recognition or the like), or others besides.

In any case, at least an ID datum must be included among the data exchanged by the medical machine 2 with the remote unit, perhaps for example by the control unit 4 (but also from the web server 11 or even from the central control program 12).

The machine 2 will include a list of predefined identification data, to each item of which a respective access authorisation to the medical machine will be associated.

The access authorisations define the remote interventions the user can make on the medical machine. They comprise at least the authorisation to passive access to vision, i.e. to be allowed to view the web pages of the web server 11 without however being able to control any machine 2 functions, and at least permission to actively access in order to control, i.e. to actively control (i.e. change or set machine operating parameters or activate/deactivate functions) from a remote location.

In reality the access levels can be many, and can be easily customised such that each user can only view and/or intervene on the machines 2 to pre-decided extents.

Some users might only be authorised to view the GUI, while others might be authorised to view all machine data but without any authority to intervene. Others besides might have active control access only to some machine functions and not others, while still others might have total access to all machine functions both passively (viewing) and actively (controlling).

Thus levels of access can be defined, for example for medical personnel, nurses, technical staff controlling and maintaining the machine, or net system administrators.

On each connection, after the ID procedure, the control unit 4 (or as mentioned the web server 11 or the central control program 12) will verify access authorisation and will assign the user the level of access afforded to him or her. In other words, according to the type of protected access afforded, the remote user will be able to operate at least in a solely monitoring mode (having access to all the above-mentioned data without any power to interact actively with the medical machine) and a full machine control mode (where she or he will be able to interact and command the medial machine as if standing right before it). Obviously situations can be set up in which there is only a partial control modality, i.e. only some of the functions normally controlled by acting directly on the machine.

Note however that the control unit 4 of the medical machine is predisposed to selectively inhibit the remote access and control means 10 from taking and/or maintaining control of at least some of the predetermined number of medical machine functions in particular not only according to the ID of the user, but also (or even only) according to the operating configuration (or modality) of the machine itself.

In other words the medical machine 2 will operate in a plurality of different operating configurations (or modes), some of which will be more or less critical for security.

With reference to known-type medical machines for extracorporeal blood treatment, some of the above-mentioned various operating configurations can be described: at least a first operating configuration for machine start-up and automatic check of its operability; a priming operating configuration of the hydraulic circuit, which consists in the preparatory stage of the machine before treatment in which air is removed from the piping; a disinfecting/cleaning operating configuration (for example chemical and/or thermal) of the hydraulic circuit; a rinsing operating configuration of the hydraulic circuit; an operating configuration in which treatment fluid is prepared (for example a dialysis fluid) up to reaching the desired characteristics of the fluid, etc.

There is also an operating configuration in which the medical machine is set up for use, i.e. all single-use disposable components are applied, such as the filter and the blood circuit. There is also a blood circuit priming operating configuration, and configurations for other disposable circuits too.

There is also an operating configuration of connecting the patient to the machine and a treatment configuration followed by the patient blood return operating configuration (rinseback) after finishing the treatment, and finally the disconnection of the patient.

Further machine configurations can be identified, i.e. a configuration in which the disposable components are removed, or one in which the liquids still present in the circuits are eliminated, as well as other operating configurations connected with various further procedures such as calibrations, maintenance or more besides.

Merely by way of example the critical operating configurations for questions of security are the stage of connecting and the stage of disconnecting the patient to and from the machine before and after treatment, as well as the stage of treatment true and proper and the stage of rinse-back, in which the residual blood is returned to the patient.

Should the control unit 4 detect that the machine is in one of the operating configurations defined as critical for security, the control unit itself would be empowered to prevent the remote means for access and control 10 to take control of the medical machine or, in a case in which a remote unit 7 is controlling, the control unit 4 would exclude any possibility of proceeding with said control/intervention from remote.

All of the above is true whatever the type of the individual in remote connection (doctor, technician, etc. . . . )

Thus according to the operative configuration, the control unit 4 is automatically able to detect a situation of potential danger and will prevent access by a remote user whatever her or his authorisation level.

This mode of operation thus enables potentially dangerous situations to be accounted for, in which sending commands to the machine would be preferable or it would be physically necessary to be present in the place where the medical machine is located in order to take account of situations which cannot be perceived from a remote position (interactions with the patient such as disconnection or connection, or the state of the patient during treatment etc.). It should be noticed that in general, in order to be able fully to exploit the above-described functionalities, the remote unit 7 will be provided with a respective device 8 for entering at least command data (in this case too it might be a keyboard, a mouse or a touch screen or another suitable system) and also a display screen 9 for viewing at least a part of the information relating to the fluid treatment means 3 and in general the graphic user interface substantially in real-time (i.e. with transmission delays of a few seconds).

Obviously there will be connecting means 16 present for setting the remote unit 7 in communication with the medical machine 2 for fluid treatment for exchange of data.

In general the connecting means 16 are of known type and comprise a computer network, for example an internet network and/or an Ethernet and/or a wireless network, for setting the remote unit 7 (any unit 7 connected to the network) in communication with a the means for fluid treatment 2 (i.e. the desired machine from among all the machines connected up to the network and therefore accessible).

The means 16 shall be provided with receiving and transmitting modules able to receive a request signal coming from the remote unit 7 and transmitting, following the reception, a transmission signal destined for the remote processor and incorporating the data and/or one or more of the web pages present on the web server 11 managed by the processing unit 4.

To this end there will also be special communication ports, network cards and/or modems not further described herein inasmuch as they are of absolutely known type in the sector.

Figure 5:
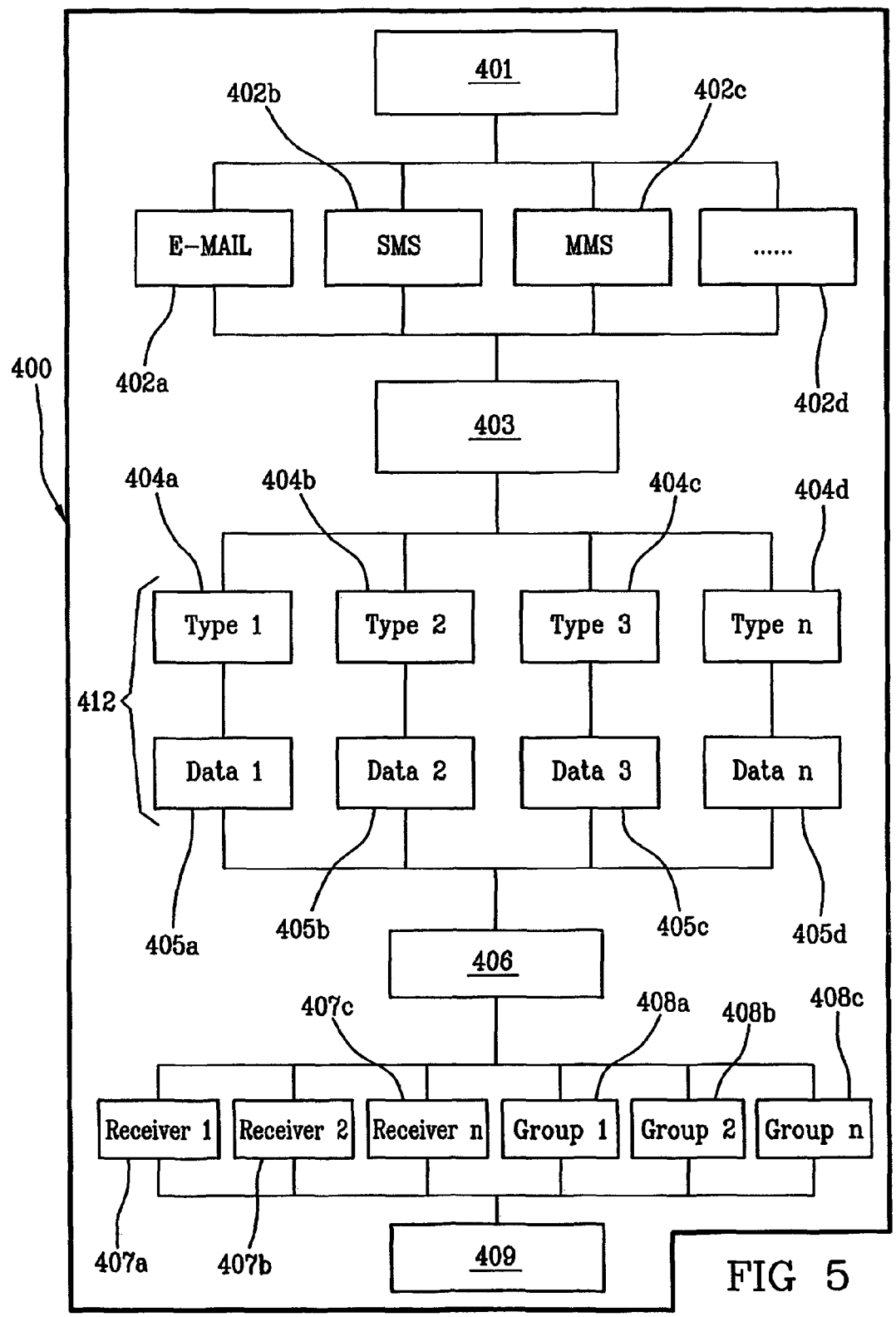
FIG. 5 is a schematic view of a form for sending a signalling message of the machine of FIG. 4.

The medical machine 2 will advantageously be provided with at least a module 400 for the management and despatch of a signal message containing data relating to means for fluid treatment. This module, which can for example be a software program stored in the memory and run by the control unit 4, is schematically illustrated in FIG. 5.

Means 401 for selecting a format 402a, 402b are present for sending a signal message. In general the means 401 select the format from among a plurality of predefined formats 402a, 402b, 402c, 402d either automatically or manually.

Purely by way of example, possible formats (which can be of many types) comprise e-mail messages, SMS text messages, MMS or others besides.

The selection of the format can be automatic and obviously predefined, in which an alarm (for example a pump failure), or a notification (for example N days since a maintenance intervention) have been configured such that the control unit 4 uses the format without any need for the intervention of an operator, thus guaranteeing top-level reliability of notification in predetermined situations.

In the case of a manual selection (the operator can decide at any moment), the user interface 300 will comprise a window exhibiting a predetermined number of graphic elements 413, such as pictograms and/or logograms (for example in the form of touch buttons), each relating to a format for sending a signalling message.

The user interface, which in the specific case comprises the display of the graphic user interface (i.e. associated to the medical machine), can comprise, in other embodiments, a remote device, either additionally or alternatively to the local display. It is thus possible to include both the use of a local graphic user interface and the use of a remote graphic user interface (for example such as the one described herein above). The remote user interface might be able to is reproduce another user interface, different from the one viewed on the local display, for example a further interface which can be generated by the control unit of the medical machine 2.

In other terms, the control unit 4 will predispose a predetermined number of pages (for example web pages) corresponding to different user interfaces and the user can shift among the pages either directly on the medical machine 2 in question, or remotely with a common terminal and further the pages viewed on the machine and on one or more of the connected remote terminals can be different from one another (i.e. each user can view the page of interest to him or her).

Looking at FIG. 6a, a plurality of touch buttons 413 can be seen, each of which relates to a different format. The nurse, doctor or maintenance technician alike can decide at any moment during operation (even not in the presence of alarms or specific predefined situations) to generate a particular message, by sending a predetermined number of data to predefined addressees (as will better emerge in the following description).

The manual selection can be done differently, for example by using a keyboard or a mouse and clicking on the respective touch button.

Alternatively and advantageously a touch screen can be used by directly pressing the corresponding touch button such as to make the operation more intuitive, rapid and simple.

The module 400 further comprises means 403 for generating contents for the signal message.

The contents 412 are usually constituted by the type of contents 404a, 404b, 404c, 404d and by the actual information 405a, 405b, 405c, 405d relating to the medical machine in general and specifically to the means 3 for fluid treatment.

The contents 412 are principally determined by means of selection from among a plurality of types of predefined contents 404a, 404b, 404c, 404d.

In general, following each selection relating to the format 402a, 402b, 402c, 402d of the signalling message, the user interface 300 will present a plurality of visual representations 410, for example pictograms or logograms (optionally, as in this case, in the form of touch buttons), each relating to a type of contents 404a, 404b, 404c, 404d of the signal message (see FIG. 6b).

In general, though not necessarily, the visual representations 410 will be different according to the format 413 of the message selected.

It is clear that an e-mail has a different capacity of information in comparison with an SMS or an MMS message.

In particular, the means 403 for generating the contents enable a selection to be made from among one or more visual representations 410 in order to determine the type of contents of the message.

As in the preceding situation, the means 403 for generating contents of the signalling message comprise a device 5 for entering commands with the aim of enabling selection of one or more types of predefined contents 404a, 404b, 404c, 404d.

The device for entering commands 5 will advantageously comprise at least a touch screen associated to the display 6; the touch screen enables the user to select the types of contents 404a, 404b, 404c, 404d from the user interface 300, selecting by contact with or proximity to the respective visual representations 410.

It is stressed that several types of predefined contents can be associated to each format of the signalling message.

When, for example, the means 401 for determining a format select an e-mail format 402a, the means 403 for generating signal message contents predispose the contents 412 in the form of one or more attached files to the e-mail message.

The plurality of types of contents 404a, 404b, 404c, 404d comprise, for example, a copy (screenshot) of the current graphic user interface 300, as visualised by the machine 2 at the moment when the selection of the type of attached file was sent, and its time of despatch.

Other types of contents (enclosed with the e-mail) can be files or models containing specially-sampled n machine parameters, which can be preconfigured and completed with the current data at the moment of selection of the type or at the moment the message is sent; alternatively, or in addition, files or blocks relating to the configuration of the medical machine itself (data relating to the cards mounted on the machine, the release of the various programs etc) can be sent, and/or the diagnostic data (alarms set off during the time period, tables summarising the machine status, etc) or apparatus check-ups.

It will be understood that the types of contents will be different and will be sent according to the needs of the moment.

It is also clear that a maintenance technician will wish to see the machine check-up data or configuration information; the doctor will want to check the medical machine parameters during its functioning, i.e. the graphic user interface when a problem crops up during treatment.

Note that at the moment when the means 403 generating the contents of the signal message determine the type of contents, the information 405 in the contents of the message will optionally be automatically uploaded to the signal message at the same time as the selection of the type of contents of the control unit.

In other words, when the operator decides to send, for example the graphic user interface by e-mail, the medical machine, i.e. the control unit 4, can automatically load the data relating to the moment it was decided to send the e-mail.

Equally, at the moment that the operative machine parameters are selected for mailing, the machine automatically acquires the parameters and enters them into the format, completing the contents 412 of the signal message.

It is therefore evident that, selected by one of the predefined formats, the contents which are associated to the format for completing the contents 412 of the signal message will vary from moment to moment, thus enabling a photograph of a topical moment to be made at any time for future analysis.

Finally, the form 400 comprises means 406 for selecting at least an addressee to whom to send the message.

The user interface 300 exhibits, usually, a predetermined number of graphical representations 414, 415, for example pictograms and/or logograms (in this case too they can be touch buttons), each of which relates to an addressee's identification address, or relative to a group of identifying addresses of a list of addressees.

In other words the means for selecting an addressee 406 enable one or more addressees of the signal message to be chosen from a list of identifying addresses 407a, 407b, 407c, 408a, 408b, 408c.

As can be seen in FIG. 5, single addressee-identifying addresses (e-mail addresses, cell-phone numbers, etc.) can be created, i.e. lists of addressees a same message can be contemporaneously sent (doctors, technicians etc.).

This operation too, like the preceding ones, can be done manually by an operator, i.e. automatically when the predetermined conditions occur.

Selection can be done via a keyboard, mouse or even a touch-screen, as mentioned herein above. Selection can be done via the local user interface or the remote user interface.

Note that the medical machine is further provided with means 411 for configuring the form 400. The means 411 for configuring enable the list of identifying addresses to be notified via the signal message to be set up; otherwise the means 411 for configuring enable one or more e-mail servers to be established for sending the signal message and also to predispose a common standard text, possibly editable, to be inserted as the text of the signal message in addition to the above-mentioned further data and information.

The means 411 for configuring (for example a program code) can be graphically represented in a window of the user interface 300 such as to be able to intervene with the aim of predisposing the configuration modifications of the module 400 with the above-mentioned data entering device 5 (mouse, touch screen, etc.).

The machine further comprises a system memory 416; at least the data 405a, 405b, 405c, 405d included in the signal message are sent from the control unit 4 to the system memory 416 for conserving the data and possibly for consulting it later on.

Also to be noted is the fact that the means 401 for selecting the format, the means 403 for generating the contents of the signal message, the means 406 for selecting the addressee (but possibly also the means 411 for configuring the form 400) are remotely activatable via the graphic user interface 300 accessible through the web pages published by the web server 11. It is further possible to activate the means 401, 403, 406, 411 via a web page published by the web server on the remote display and different to the graphic representation on the local interface user 300.

By doing this, the functions of the module 400 are also remotely usable without any need for the operator to be present in the place where the medical machine 2 is actually working.

In this way a technician, or any other authorised person, can send messages containing the most relevant or significant or interesting information to any of the personnel whose addresses are stored on the user interface 300 (for example to him- or herself and to other operators), including directly from a remote position without there being any need to be present in the machine locus.

Sending the message (especially the e-mail message) might for example be generated by the following situations:
  pressing the button (i.e. e-mail 402a) present on the graphic user interface 300 (a nurse, seeing the moment of difficulty, can be assured that the information relating to the problem will not be lost but will be received by a technician; a maintenance technician can send some data of interest to the machine or send it to another technician for consultation purposes);
  pressing the button from a remote location (i.e. e-mail 402a) present on the graphic user interface 300 published on the web pages of the web server 11 (with the graphic user interface published on the web pages of the web server being possibly different from the graphic user interface 300 shown on the local display);
  on one or the predetermined events occurring with automatic sending of the message (serious alarms or malfunctioning will lead to a message being sent bearing information which will be automatically stored in the system memory);
  when the predetermined deadline has passed (for example every N days, or every N hours of use of the medical machine, or even every N treatments performed by the medical machine);
  fewer than N days until the next maintenance check.

The invention leads to important advantages.

Primarily, the proposed system and methodology for the management of signals enables message to be sent which are of a different nature, at any moment of operation of the machine.

In other words, the machine is configurable for automatic sending of certain types of pre-organised messages when certain special events occur, but it can be used at any time for sending messages of a different nature (e-mails, SMS messages, local network messages . . . ) according to the needs of the operator, nurse or technician.

It is extremely simple to send a plurality of messages of a different nature to different addressees, by a touch-screen manual selection, very simple to understand and use.

For example, when a dangerous situation for the patient arises, a nurse can send messages with certain contents to a doctor and, at the same time, send different messages with contents of a different nature to a technician such that the technician can receive instructions relating both to the treatment and to the technical interventions on the machine.

Further, the form 400 is also remotely accessible such that the implemented system can be exploited without having necessarily to be present in the machine locus.

Worthy of note is the fact that all the information sent are stored in the central server such that a situation of danger/warning/interest is subject to a snapshot and the relative data are accessible at any moment thereafter.

Figure 3:
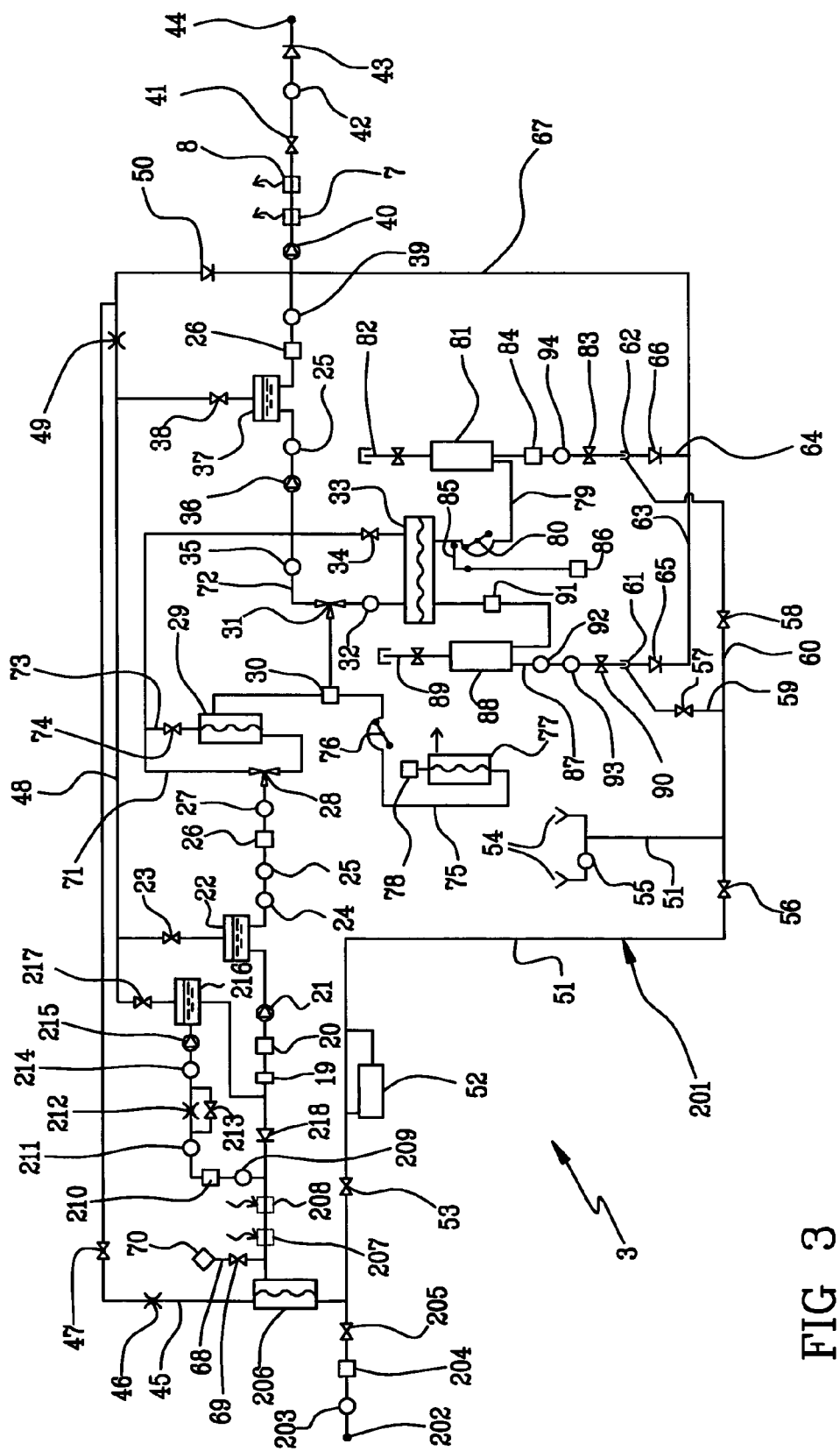
Figure 4:
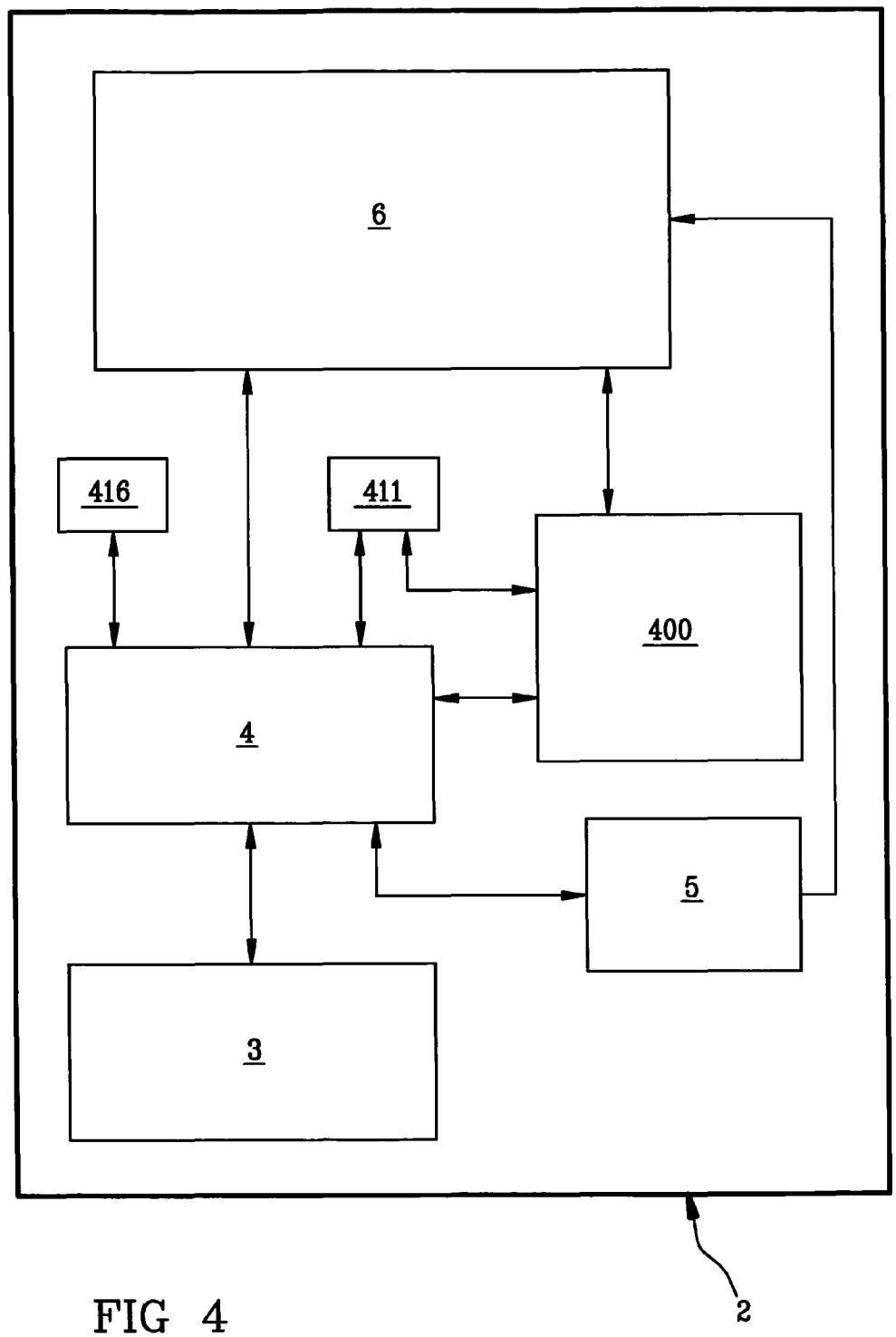
FIG. 4 is a further schematic view of a medical machine of the present invention.

The follow are the numerical references in FIG. 3.
  201 Hemodiafiltration apparatus
  202 Water inlet
  203 Inlet pressure sensor
  204 Inlet pressure regulator
  205 Inlet check valve
  206 Ultrafilter for water at inlet
  207 First heat exchanger 208 Second heat exchanger
209 Pressure sensor at inlet of the heating and degassing circuit
210 heater
211 temperature sensor in the heating and degassing circuit
212 degassing choke
213 bypass valve of degassing choke
214 pressure sensor for control of degassing pump
215 degassing pump
216 first gas-liquid separator in heating and degassing circuit
217 first degassing valve
218 check valve for the heating and degassing circuit
19 pressure regulator at outlet of heating and degassing circuit
20 on-line preparation device for dialysate with water and concentrates
21 fresh dialysate movement pump
22 second gas-liquid separator for the fresh dialysate
23 second degassing valve
24 sensor system for measuring some parameters (in particular temperature, conductivity and pH) of the fresh dialysate
25 protection system for fluid balance in excess in control system
26 fluid balance control system
27 pressure sensor at inlet of dialysate ultrafilter
28 first bypass valve for bypass of dialysate ultrafilter
29 dialysate ultrafilter
30 connection for a disposable line for replacement fluid
31 second bypass valve for dialyser bypass
32 pressure sensor at dialyser inlet
33 dialyser
34 check valve at dialyser outlet
35 pressure sensor at dialyser outlet
36 used dialysate movement pump
37 third gas/liquid separator for used dialysate
38 third degassing valve
39 sensor system for measuring some parameters (in particular temperature, conductivity, pressure and presence of blood loss) of the used dialysate
40 aspiration pump for stabilising pressure downstream of the fluid balance control system
41 normally-open check valve at outlet
42 outlet pressure sensor
43 outlet check valve
44 outlet end connected to a drainage
45 water ultrafilter flushing line
46 flushing line choke
47 check valve on flushing line
48 breather valve connected to the breathers of the various gas-liquid separators
49 choke connected to the breathers of the various gas-liquid separators
50 check valve operating on a tract of line in common with the flushing line and the breather circuit
51 recycling circuit for complete thermal or chemical disinfection circuit
52 source of a chemical disinfectant including the means for supplying the disinfectant
53 first check valve for enabling recycling during thermal or chemical disinfection
54 pair of connectors for dialyser bypass during thermal or chemical disinfection
55 dialyser bypass flow sensor
56 second check valve to enable recycling during thermal or chemical disinfection
57 first check valve for enabling supply of disinfectant to the first discharge port of the priming fluid
58 second check valve for enabling supply of disinfectant to the second discharge port of the priming fluid
59 first branch for disinfection of the first discharge port of the priming fluid
60 second branch for disinfection of the first discharge port of the priming fluid
61 first discharge port of the priming fluid
62 second discharge port of the priming fluid
63 first discharge line of priming fluid
64 second discharge line of priming fluid
65 first check valve
66 second check valve
67 line conjoining the first and second priming fluid discharge lines with the used dialysate line
68 line connecting with the atmosphere upstream of the heating and degassing circuit
69 check valve of the connecting line with the atmosphere
70 air filter
71 first bypass line (dialysate ultrafilter bypass)
72 second bypass line (dialyser bypass)
73 flushing line of the dialysate ultrafilter
74 check valve of the dialysate ultrafilter flushing line
75 replacement fluid supply line
76 replacement fluid movement pump
77 replacement fluid pump ultrafilter
78 replacement fluid breather system
79 arterial line
80 blood pump
81 arterial chamber
82 arterial chamber service line
83 arterial clamp
84 arterial line access site
85 anticoagulant supply line
86 anticoagulant source
87 venous line
88 venous chamber
89 venous chamber service line
90 venous clamp
91 venous line access site
92 air bubble sensor
93 blood presence sensor (patient sensor)
94 hemoglobin or hematocrit sensor, or blood volume sensor.

The invention claimed is:
1. A medical machine for extracorporeal blood treatment, comprising:
  means for treatment of a fluid including:
    a predetermined number of sensors for detecting functioning parameters of the medical machine, and
    a predetermined number of actuators for intervening in order to modify the functioning parameters of the medical machine;
  a control unit sending command signals to the actuators and receiving information from the sensors for setting and determining an operative configuration of the machine, the control unit being further configured to generate at least a local user interface;
  a display for viewing the local user interface and for exhibiting at least a part of the information received from the control unit and relating to the means for fluid treatment;
  a module for managing and sending signal messages containing information relating to the means for fluid treatment;

wherein the module comprises:
  means for determining a sending format for sending a signal message;
  means for generating contents of the signal message, the contents being determined by selection from among a plurality of types having predefined contents and comprising information relating to the means for fluid treatment;
  means for determining at least an addressee to whom to send the signal message, and
wherein
the means for generating contents of the signal message are configured to complete the contents of the signal message with current data substantially at the moment when the signal message is sent.

2. The machine of claim 1, wherein the determination of the contents of the signal message is done by a manual selection between predefined types of contents.

3. The machine of claim 1, wherein at least a part of the predefined types of contents comprises one or more visual representations which can be viewed on the local user interface.

4. The machine of claim 1, wherein the means for generating contents of the signal message comprise a device for entering commands for enabling a selection of one or more of the predefined types of contents and wherein the device for entering commands comprises at least a touch screen associated to the display, the touch screen enabling a selection on the local user interface of the types of contents, by a user by touching or by proximity with one or more visual representations.

5. The machine of claim 1, wherein the plurality of types of contents comprises a type of content chosen in the group including at least a copy of the local user interface and a configuration file and diagnostic data of the medical machine.

6. The machine of claim 1, wherein the means for determining the sending format select the sending format either automatically or manually from among a plurality of predefined sending formats, the types of contents being different according to the sending format selected from among the plurality of predefined sending formats.

7. The machine of claim 1, wherein the local user interface comprises a graphic user interface comprising a visual representation for each type of predefined contents.

8. The machine of claim 1, further comprising means for configuring the module for sending the signal message, the means for configuring enabling a setting-up of a list of identifying addresses of addressees who can receive the signal message.

9. The machine of claim 8, wherein the list of identifying addresses is viewed on the local user interface.

10. The machine of claim 8, wherein the means for configuring the module enable one or more e-mail servers to be established for sending the signal message.

11. The machine of claim 8, wherein the means for configuring the module enable an editable common standard text to be set up to be included in a signal message.

12. The machine of claim 1, wherein the means for determining an addressee enable one or more addressees to be selected for the signal message, from a list of identifying addresses of addressees.

13. The machine of claim 1, wherein the plurality of sending formats for sending a signal message comprises at least an e-mail form and an SMS form.

14. The machine of claim 13, wherein when the means for determining a sending format select an e-mail form, the means for generating a content of the signal message predispose the contents in a form of one or more file enclosures with the e-mail.

15. The machine of claim 1, wherein the local user interface comprise a predetermined number of graphic elements each relating to a sending format for sending the signal message, the means for determining the sending format enabling a manual selection of one of the graphic elements for determining the sending format to be sent.

16. The machine of claim 1, wherein the local user interface comprise a plurality of visual representations each relating to a type of contents of the signal message, the means for generating contents enabling a manual selection of one or more of the visual representations for determining a typology of contents of the message.

17. The machine of claim 1, wherein the local user interface comprise a predetermined number of graphic representations each relating to an identifying address of an addressee or a group of identifying addresses of a group of addressees to whom to send the message.

18. The machine of claim 1 further comprising a web server operatively cooperating with the control unit and a predetermined number of web pages publishable by the web server, the web pages being accessible from a remote position via connecting means and being consultable via a web browser, at least a web page reproducing the local user interface.

19. The machine of claim 18, wherein at least a web page reproduces the local user interface shown on the display of the medical machine, the web pages further publishing a plurality of further data relating to the medical machine.

20. The machine of claim 18, wherein the web server is an internet web server which is consultable from a remote position by means of a web browser.

21. The machine of claim 18 comprising remote access and control means for enabling a reproduction on the web pages of the web server of the local user interface shown on the display.

22. The machine of claim 21, wherein the remote access and control means enable reproduction of the local user interface in the web pages, substantially in real-time.

23. The machine of claim 21, wherein the reproduction of the local user interface is updated at an each predetermined time interval or at each predetermined change in at least a parameter represented in the user interface.

24. The machine of claim 23, wherein the user interface is sub-divided into a plurality of regions and that the updating of the reproduction of the user interface includes the reproduction of each region of the user interface being updated at each predetermined change of at least a parameter shown in the region without updating regions where a change has not occurred.

25. The machine of claim 18, wherein the means for generating the contents of the signal message are activated remotely, by acting on the user interface which is accessible via the web pages published by the web server, the means for determining the sending format for sending a signal message being activated remotely by acting on the user interface, selecting respective graphic elements each associated to a respective sending format, the means for determining an addressee being activated remotely by acting on the user interface to select a graphic representation corresponding to an identifying address or a group of identifying addresses.

26. The machine of claim 1, wherein the means for generating contents of the signal message enable determining a type of contents by selection, the information present in the contents of the message being automatically inserted into the signal message by the control unit, simultaneously with selection of the type of contents.

27. The machine of claim 1 further comprising a system memory, at least the information included in the signal message being sent by the control unit to the system memory for a subsequent consultation.

28. A medical machine for extracorporeal blood treatment, comprising:
   means for treatment of a fluid including:
      a predetermined number of sensors for detecting functioning parameters of the medical machine, and
      a predetermined number of actuators for intervening in order to modify the functioning parameters of the medical machine;
   a control unit sending command signals to the actuators and/or receiving information from the sensors for setting and/or determining an operative configuration of the machine, the control unit being further destined to generate at least a local user interface;
   a display for viewing the local user interface and for exhibiting at least a part of the information received from the control unit and relating to the means for fluid treatment;
   a module for managing and sending signal messages containing information relating to the means for fluid treatment, wherein the module comprises:
      means for determining a sending format for sending a signal message, the local user interface comprising a predetermined number of graphic elements each relating to the sending format for sending the signal message, the means for determining the form enabling a manual selection of one of the graphic elements for determining the form to be sent;
      means for generating contents of the signal message, the contents being determined by selection from among a plurality of types having predefined contents and comprising information relating to the means for fluid treatment, the local user interface comprising a plurality of visual representations each relating to a type of contents of the signal message, the means for generating contents enabling a manual selection of one or more of the visual representations for determining a typology of contents of the message, the types of contents being different according to the sending format selected from among the plurality of predefined sending formats;
      means for determining at least an addressee to whom to send the signal message enabling one or more addressees to be selected for the signal message, from a list of identifying addresses of addressees, the types of contents of the signal message being different according to the one or more addressees selected from the list of identifying addresses of addressees.

29. The machine of claim 1, wherein the means for generating contents of the signal message are further configured to include one or more specially-sampled machine parameters in the contents of the signal message in addition to the current data.

30. A medical machine for extracorporeal blood treatment, comprising:
   means for treatment of a fluid including:
      a predetermined number of sensors for detecting functioning parameters of the medical machine, and
      a predetermined number of actuators for intervening in order to modify the functioning parameters of the medical machine;
   a control unit sending command signals to the actuators and receiving information from the sensors for setting and determining an operative configuration of the machine, the control unit being further configured to generate at least a local user interface;
   a display for viewing the local user interface and for exhibiting at least a part of the information received from the control unit and relating to the means for fluid treatment;
   a web server operatively cooperating with the control unit and a predetermined number of web pages publishable by the web server, the web pages being accessible from a remote position via connecting means and being consultable via a web browser, at least a web page reproducing the local user interface;
   remote access and control means for enabling a reproduction on the web pages of the web server of the local user interface shown on the display, wherein the remote access and control means enable reproduction of the local user interface in the web pages, substantially in real-time;
   a module for managing and sending signal messages containing information relating to the means for fluid treatment;
   wherein the module comprises:
      means for determining a sending format for sending a signal message;
      means for generating contents of the signal message, the contents being determined by selection from among a plurality of types having predefined contents and comprising information relating to the means for fluid treatment;
      means for determining at least an addressee to whom to send the signal message.

* * * * *